United States Patent [19]

Gores et al.

[11] Patent Number: 4,475,888

[45] Date of Patent: Oct. 9, 1984

[54] ANTERIORLY JOINED DENTAL TRAYS

[76] Inventors: Kenneth W. Gores, Bellevue Medical Dental Center, 1026-112th St. NE., Bellevue, Wash. 98004; Carolyn C. Gores, 827 Lake St. South, Kirkland, Wash. 98023

[21] Appl. No.: 369,783

[22] Filed: Apr. 19, 1982

[51] Int. Cl.$^3$ ............................................. A61C 9/00
[52] U.S. Cl. ...................................... 433/42; 128/136
[58] Field of Search ........................... 433/39, 42, 80; 128/62 A, 136; 604/37, 316

[56] References Cited

U.S. PATENT DOCUMENTS

| | | | |
|---|---|---|---|
| 3,536,069 | 10/1970 | Gores | 128/136 |
| 3,955,281 | 5/1976 | Weitzman | 433/80 X |
| 4,173,505 | 11/1979 | Jacobs | 128/136 X |
| 4,356,599 | 11/1982 | Larson et al. | 24/16 PB |
| 4,376,628 | 3/1983 | Aardse | 433/42 X |

Primary Examiner—Robert P. Swiatek
Attorney, Agent, or Firm—Ford E. Smith

[57] ABSTRACT

A pair of arcuate concavo-convex trays formed of a plastic foam material shaped to be inserted into the mouth and to encase both the upper and lower jaws. The trays are normally disposed in mirror-like opposition and joined anterior-to-anterior by a bridge member adapted to bow, bend or fold so that the exterior surfaces of the trays are juxtaposed bottom to bottom. The trays are used to receive and contain a medicament for topical application to a person's teeth, fluoride gel being a typical topical material.

4 Claims, 4 Drawing Figures

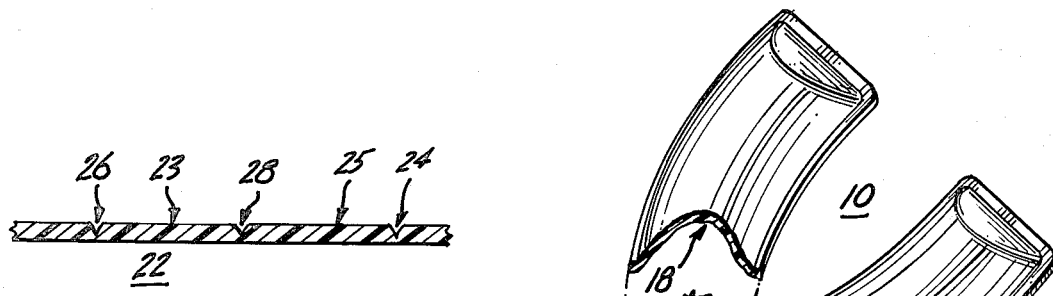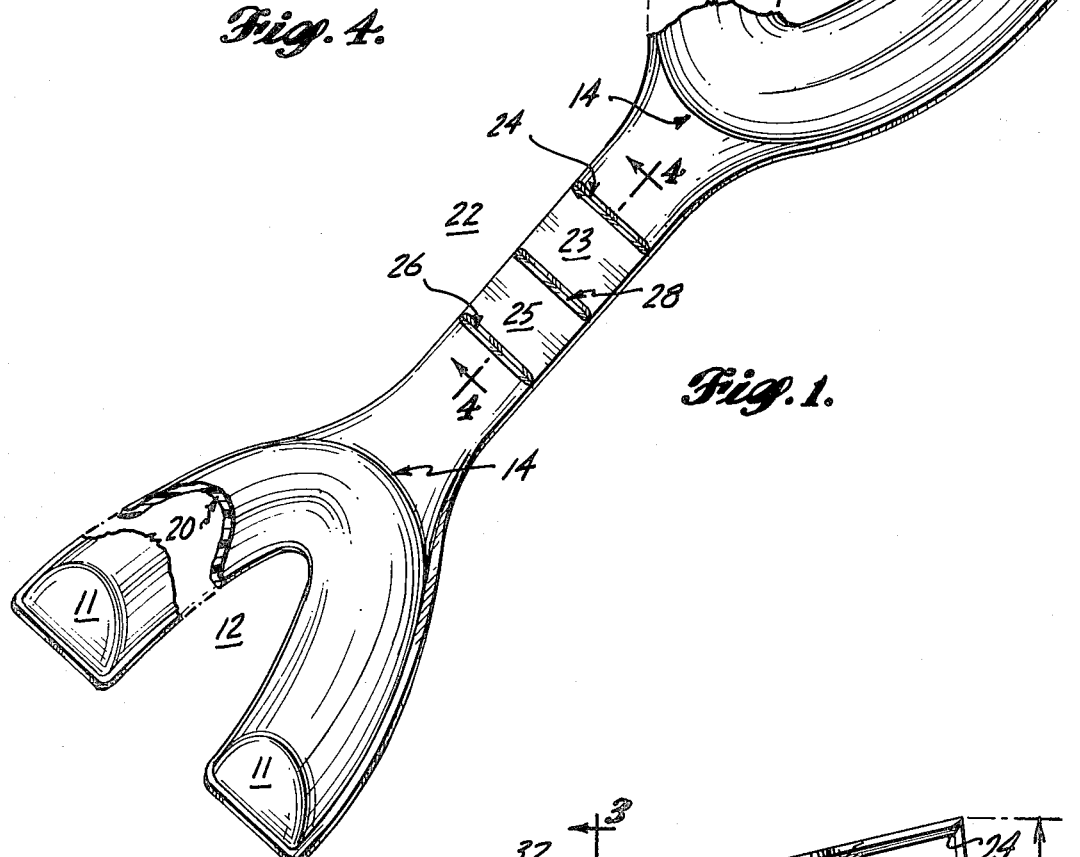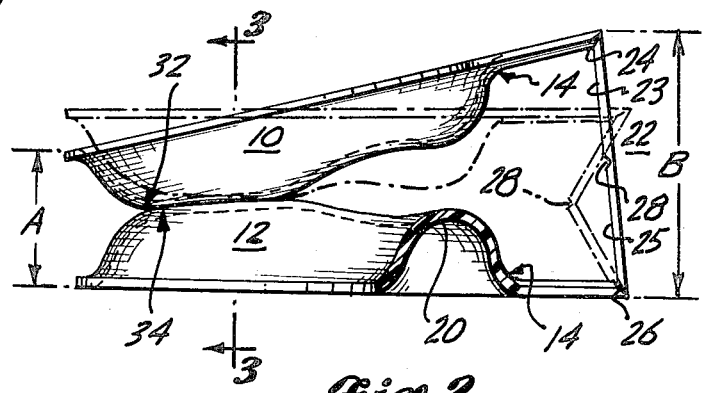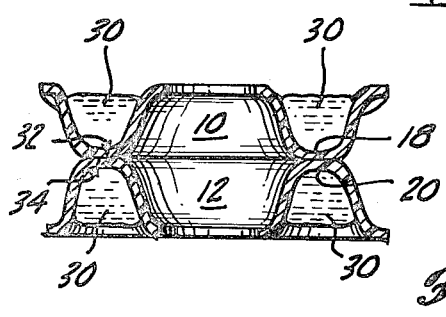

1

ANTERIORLY JOINED DENTAL TRAYS

SUMMARY OF THE INVENTION

In this invention a pair of U-shaped trays are joined anteriorly in mirror-like relation by a bridging member that is bendable or foldable to permit the trays to be disposed bottom-to-bottom for insertion into a dental patient's mouth. By making the bridging member of a predetermined length greater than the combined thickness of the posterior portions of the trays, the apparatus assumes a wedge-like shape to facilitate placement in the mouth. A medical gel is deposited in the trays and is worked around and between the teeth in each tray by grinding and pumping action between his jaws produced by the patient. The device is usually manufactured by molding a thermoplastic foam sheet material for low cost production and to economically permit disposal after a single use.

A double-tray dental apparatus as shown in this applicant's U.S. Pat. No. 3,536,069 has been extensively produced and used as a disposal device. In that instance the trays are normally arranged posterior-to-posterior with hinge means extending between the buccal exteriors of the trays. In this application applicant seeks to simplify production, to reduce costs, and to use less expensive material to produce a pair of trays. So far as applicant knows his invention is structurally distinguishable from the dental tray of U.S. Pat. No. 3,955,281 in that the latter is unknown to be used in pairs or even so used to be joined anteriorly. A disposable device employing a posteriorly joined pair of trays produced by Sultan Dental Products of Englewood N.J. is known but is to be distinguished by reason of the tray joinder elements extending between the posterior and not the anterior portions of paired trays. Copies of these referenced sources are included herewith.

DESCRIPTION OF THE DRAWINGS

FIG. 1 is perspective view of the exterior of an anteriorly bridged pair of dental trays;

FIG. 2 is a side view of the pair of trays folded for insertion into a person's mouth;

FIG. 3 is a cross-section on line 3—3 of FIG. 2;

FIG. 4 is a cross-section on line 4—4 of FIG. 1.

THE SPECIFICATIONS

In the preferred form of the invention, as shown in FIG. 1 of the drawings, a pair of arcuate dentition trays 10 and 12 are normally manufactured in an opposed relationship wherein their anterior portions 14 are respectively in a mirror-like arrangement each looking toward the other.

Each tray is concavo-convex in cross-section to provide U-shaped troughs 18 and 20 that engage and cup the upper and lower teeth of a patient. These troughs receive medication material pertinent to the topical treatment being conducted. Usually the material is a fluoride gel 30.

The arcuate trays 10 and 12 are joined by bridging member 22 which is usually formed of the same material as and integral with the trays. Bridging member 22 has a pair of spaced-apart fold or score lines 24 and 26. It may also have a third score line 28 intermediate lines 24, 26 for a purpose to be described later herein. Score line 28 may be more shallow or less prominent than lines 24, 26.

The use of the trays to medically treat the upper and lower jaws and teeth of a person usually involves a topical application of a fluoride gel 30 containing a fluoride compound. This gel is viscous and normally adheres to the walls of the trough.

The gel material 30 is shown in both the upwardly open trough 10 and during use in the inverted trough 12 as best seen in FIG. 3. When the bridge member has been folded to bring the convex sides of the trays into juxtaposition (see FIG. 2) the apparatus is ready for insertion into the mouth.

The combined length of the bridge segments 23 and 25 being the distance B (see FIG. 2) between score line 24 and 26 is such that when the bridge member 22 is folded at 24 and 26 as shown in FIG. 2, the anterior tray portions are not in contact whereas contact can occur between the more remote or posterior convex tray surfaces 32 and 34. The two trays are disposed wedge-like as shown and have a relatively lesser dimension A. In this fashion introduction of the trays deeply into a person's mouth to encase the posterior molars is facilitated. When the mouth is then closed, forcing the anterior portions of the trays together, bridge member 22 either bows or folds outward between score lines 24 and 26 or it may fold inward to an obtuse angle as indicated in dotted lines in FIG. 2.

The intermediate score or fold line 28 is preferably of lesser depth and usually localizes the folding of bridge segments 23, 25 to an inward direction. Of course, when the folded segments break outward the effect is the same. In either case the effective shortening or contracting of the distance B between folds 24, 26 readily occurs and the full tooth array of each jaw is thus disposed within and cupped by a tray.

It is intended that dental trays according to this invention be used only once and thereafter discarded. To that end it is desirable that this dental apparatus be formed or produced by a process which is high in volume relative the attendant labor and which employs readily available low cost materials. High volume production is obtained by shaping the apparatus in molds using heat-moldable sheet material. An acceptable low cost sheet material is thermoplastic. Flexible polyethylene or polystyrene in fine-cell sheet form has performed very satisfactorily. The material when molded is smooth, semi-rigid, form retaining, highly palatable. At the same time it is suitable in its molded concavo-convex tray form to retain its integrity in a person's mouth despite severe grinding and pumping actions that occur during treatment. Polystyreme foam has suitably low water absorption characteristics and is suitably inert to the medical gel with which it is used. Such plastic materials do react to the gel or breakdown or dissolve in the mouth. The preferred material is soft and spongelike thus eliminating foam inserts previously used in dental trays. It is also inexpensive. This factor coupled to high volume, low cost molding insures that the single use and throw-away disposal of the apparatus presents no economic hardship. Other plastic foams may also be useful.

Of course a reusable form of apparatus according to this invention is conceivable. In such case the molding of the opposed trays would be accomplished with more sophisticated, materials capable of numerous uses, and adaptable to the cleansing and sterilizing techniques that would be required.

When the opposed arcuate troughs and bridge are being molded, the fold lines 24 and 26 and 28 may be provided by simply line squeezing or creasing without cutting the material during molding. Or line 28 may be omitted during molding in which case the bridge member 22 simply bows outward. Or all three lines may be applied after molding.

While the troughs 10 and 12 are shown herein as having closed ends 11, for certain uses as for example in taking dental impressions, or even when produced as mouth guards the closed rear ends 11 may be omitted.

It has been observed that even with relatively thin and soft polystyrene molded trays have at the fold or hinge lines an elastic memory that tends to spread the trays apart upward and downward. This spreading of the trays aids in insuring that they follow the vertical and/or eccentric movements of the jaws and not too easily become dislodged or disarranged.

It will be apparent that in this specification is set forth a complete description of a preferred form of the invention. Alternatives and modifications will readily come to mind to those skilled in the pertinent art. All such as under a liberal application appropriate to the scope of this invention are intended to be covered by this patent.

PRIOR ART STATEMENT

Applicant is aware of the teachings of the referenced prior art which is considered not relevant or applicable singly or in combination to the claims in this patent application:

| References | | | |
|---|---|---|---|
| 2,857,909 | 10/58 | Johnson | Cl. 178/136 |
| 3,416,527 | 12/68 | Hoef | 128/260 |
| 3,536,069 | 10/70 | Gores | 128/136 |
| 3,955,281 | 5/76 | Weitzman | 32/14B |

A "Twintray" Disposable Fluoride Structure molded of a plastic foam material by SULTAN DENTAL PRODUCTS, Engleworth N.J. 07631, in which arcuate trays are flexibly joined at their posteriors is known to applicant to the extent shown in the attached tear sheet, source unknown.

We claim:
1. Dental apparatus, comprising;
    a pair of U-shaped concavo-convex, dentition troughs joined in upwardly open opposed substantially coplanar relation by a bridging member connected at each end to an anterior upper edge of one of said troughs;
    said bridging member being provided with means establishing predesignated transverse folding locations;
    said folding locations being spaced apart a distance such that, when said bridging member is folded so that said troughs are brought into bottom-to-bottom juxtaposed relation, the anteriors of said troughs are maintained spaced apart a distance greater than the combined thickness of the juxtaposed convex posterior extremities of said troughs while the convex posterior extremities may be in contact with each other for ease of introduction of the apparatus into a person's mouth.
2. The structure of claim 1, in which the means predesignating the folding locations constitute transverse scores.
3. The structure of claim 1 in which the convex surfaces of said juxtaposed trough bottoms being characterized by the absence of any protrusions thereby being capable of extensive bottom-to-bottom contact during use in patient's mouth.
4. The structure according to claim 1 in which there is a third score transverse the bridging member disposed between said folding locations.

* * * * *